United States Patent
Zimmermann et al.

Patent Number: 6,090,292
Date of Patent: Jul. 18, 2000

[54] DEVICE FOR PURIFYING SOLUTIONS CONTAINING PROTEINS AND USE OF THE DEVICE

[75] Inventors: Michael Zimmermann; Veit Otto, both of St. Wendel; Stefan Schulze, Oberursel, all of Germany

[73] Assignee: Fresenius AG, Bad Homburg, Germany

[21] Appl. No.: 09/022,709

[22] Filed: Feb. 12, 1998

[30] Foreign Application Priority Data

Feb. 12, 1997 [DE] Germany .............................. 197 05 366

[51] Int. Cl.$^7$ ..................................................... B01J 20/00
[52] U.S. Cl. ................... 210/690; 210/645; 210/500.24; 210/504; 502/403
[58] Field of Search ..................................... 210/660, 690, 210/645, 646, 908, 500.24, 504; 436/528, 531; 502/403

[56] References Cited

U.S. PATENT DOCUMENTS

| | | | |
|---|---|---|---|
| 4,411,832 | 10/1983 | Cuatrecasas et al. | 260/121 |
| 5,476,715 | 12/1995 | Otto | 428/407 |

FOREIGN PATENT DOCUMENTS

| | | |
|---|---|---|
| WO94/21363 | 9/1994 | WIPO . |
| WO95/04559 | 2/1995 | WIPO . |

OTHER PUBLICATIONS

Chemical Abstracts, vol. 93, 1980, p. 36.
Plotz, et al., "Removing Substances From Blood By Affinity Chromatography", Journal of Clinical Investigation, vol. 53, Mar. 1974, pp. 778–785.
Remillard et al., "Quantitation of Endotoxin In Products Using The Lal Kinetic Turbidimetric Assay" 1987, pp. 197–210.
Rosenbaum et al., "Current Status of Hemoperfusion In Toxicology", 1980, Clin. Toxicology, 17:493.
Shimizu et al., Enzymatic Determination of Serum–Free Fatty Acids:A Colorimetric Method, Analytical Biochemistry, vol. 107, No. 1, Sep. 1980, pp. 193–198.

*Primary Examiner*—David A. Simmons
*Assistant Examiner*—Frank M. Lawrence
*Attorney, Agent, or Firm*—Kenyon & Kenyon

[57] ABSTRACT

The invention relates to a device for purifying protein-containing solutions such as blood, blood plasma or cell culture media, where a biocompatible support material made of a plastic material, selected from the group of polyacrylates, polymethacrylates, polysulfone and polyether sulfone, is coated with albumin, which is bound by peptide binding. In addition, the invention relates to a method of producing the support material according to this invention and the use of the device.

11 Claims, 6 Drawing Sheets

DEVICE FOR PURIFYING SOLUTIONS CONTAINING PROTEINS AND USE OF THE DEVICE

FIELD OF THE INVENTION

The invention relates to a device for purifying solutions containing proteins such as blood, blood plasma or cell culture media, a method of producing a support material for said device and use of this device.

BACKGROUND OF THE INVENTION

It is already known that a number of metabolic toxins such as mercaptans, free fatty acids, unconjugated bilirubin and endotoxins of gram-negative bacteria as well as many exogenous toxins, specifically medications such as nortriptyline, amitryptiline, diazepam, bromazepam, etc., are almost completely bound to proteins in the bloodstream. They are bound preferentially to the albumin fraction of blood plasma. Because of the size of the molecules and the strong binding interaction of the protein-toxin complex, it is difficult or impossible to selectively remove from blood toxins bound to albumin by traditional blood purification methods such as hemodialysis.

However, there are already known blood purification methods with which protein-bound toxins can be removed from blood or plasma. A known method is hemoperfusion with activated carbon or ion exchange resins. These adsorber materials have measurable elimination rates for many protein-bound toxins (J. L. Rosenbaum et al. 1980: "Current status of hemoperfusion in toxicology." Clin. Toxicol. 17: 493). One disadvantage of the known adsorbents is that they have mostly nonspecific binding properties. Thus, in addition to the albumin-bound toxins, undesired hormones, growth factors and cells such as platelets are also removed, which can lead to side effects and complications.

World Patent WO 94/21363 describes a dialysis method with which albumin-bound substances can be removed from blood. An asymmetrical dialysis hollow fiber is coated with albumin essentially on the side facing away from the blood (in the porous supporting layer). In addition, the hollow fibers are rinsed with an albumin solution on the outside, with this albumin solution also being circulated through a cartridge of activated carbon or ion exchanger and passed through an additional dialyzer to remove the transported toxins from the dialysate. The toxin-laden albumin molecules of the blood are spatially separated from the toxin-free albumin molecules in the supporting layer by an internal albumin-impermeable dividing layer of dialysis fibers. The albumin-impermeable dividing layer is indispensable for the functioning of this arrangement to prevent back-diffusion of the essentially freely mobile toxin-albumin complexes and thus maintain a directional transport of toxins out of blood and into the dialysate.

To be removed from blood, the toxins must pass through the albumin-impermeable dividing layer. This is a disadvantage especially for removal of large toxin complexes such as endotoxin complexes of gram-negative bacteria, which cannot be removed from blood with the method described above. In addition, this arrangement also does not yield selective removal of substances because all substances which have such a small molecular size that they can pass through the inner dividing layer of the dialysis fibers can also be removed at the same time.

World Patent WO 95/04559 describes an arrangement with a membrane filter for eliminating toxins from protein-containing fluids, especially blood. The fluid to be purified, e.g., blood, is passed through the lumen of a hollow-fiber membrane filter around whose outside flows a purifying suspension containing solid particles to bind the toxins. The purifying suspension is kept in motion by a centrifugal pump, causing local variations in transmembrane pressure differences on the membrane filter, so there is a fluid exchange through the walls of the filter. Toxins transported with the fluid thus come in contact with the adsorbent particles, while at the same time purified fluid flows back into the blood stream. This arrangement also has the disadvantage that the toxin complexes must pass through the filter walls to be removed from the fluid to be purified.

An albumin-coated adsorber used to remove protein-bound metabolites or toxins from the blood is already known from J. of Clinical Investigation, vol. 53 (March 1974), pages 778–85. However, the known adsorber is neither hemocompatible nor steam sterilizable, so therapeutic use is impossible. Albumin is coupled via cyanogen bromide, which may adhere to the end product as an impurity and is a strong toxin even in low concentrations. The support material is also not suitable for preventing complement activation or platelet adhesion.

OBJECT OF THE INVENTION

The object of this invention is to create a device with which protein-bound toxins, regardless of size, can be selectively and effectively removed from a protein-containing solution such as blood, blood plasma or cell culture media.

This object is achieved by a device having a biocompatible support material made of plastic materials, said plastic material being selected from the following group: polyacrylates, polymethacrylates, and polysulfones, polyether sulfones having amines or amides, and being covalently coated with albumin by means of peptide binding. This support material used in the device according to this invention has especially good properties as an adsorbent.

It is especially advantageous if the albumin is bound to the plastic material by multipoint binding. This ensures the sterilizability of the adsorber.

The support material may be used in the form of bead packings or flat or hollow-fiber membranes or a film. If beads are used, they may advantageously have a diameter between 10 and 500 microns and may be packed in the form of a perfusable packing in a column having at least one inlet and one outlet.

According to an advantageous method of producing the support material to be used in the device according to this invention, a multipoint binding is created by means of a coupler reagent which activates only the carbonyl function of albumin and is then split off again. Carbodiimide or N-hydroxysuccinimide can be used in excess as the coupler reagent. The coupler reagent acts as a "catalyst" because it activates only the carbonyl function of albumin. After the reaction, the coupler reagent is split off again, e.g., as a dialkylurea in the case of carbodiimide.

The molar ratio of reactive groups of the support to the albumin concentration is advantageously 50–500:1. The coupler reagent is advantageously based on the reactive groups of the support material in an equimolar concentration up to a tenfold molar concentration. This yields multipoint binding which allows the desired steam sterilizability.

According to this invention, said device can be used to remove toxins from human whole blood, but also from human plasma or cell culture media.

Figure 1:
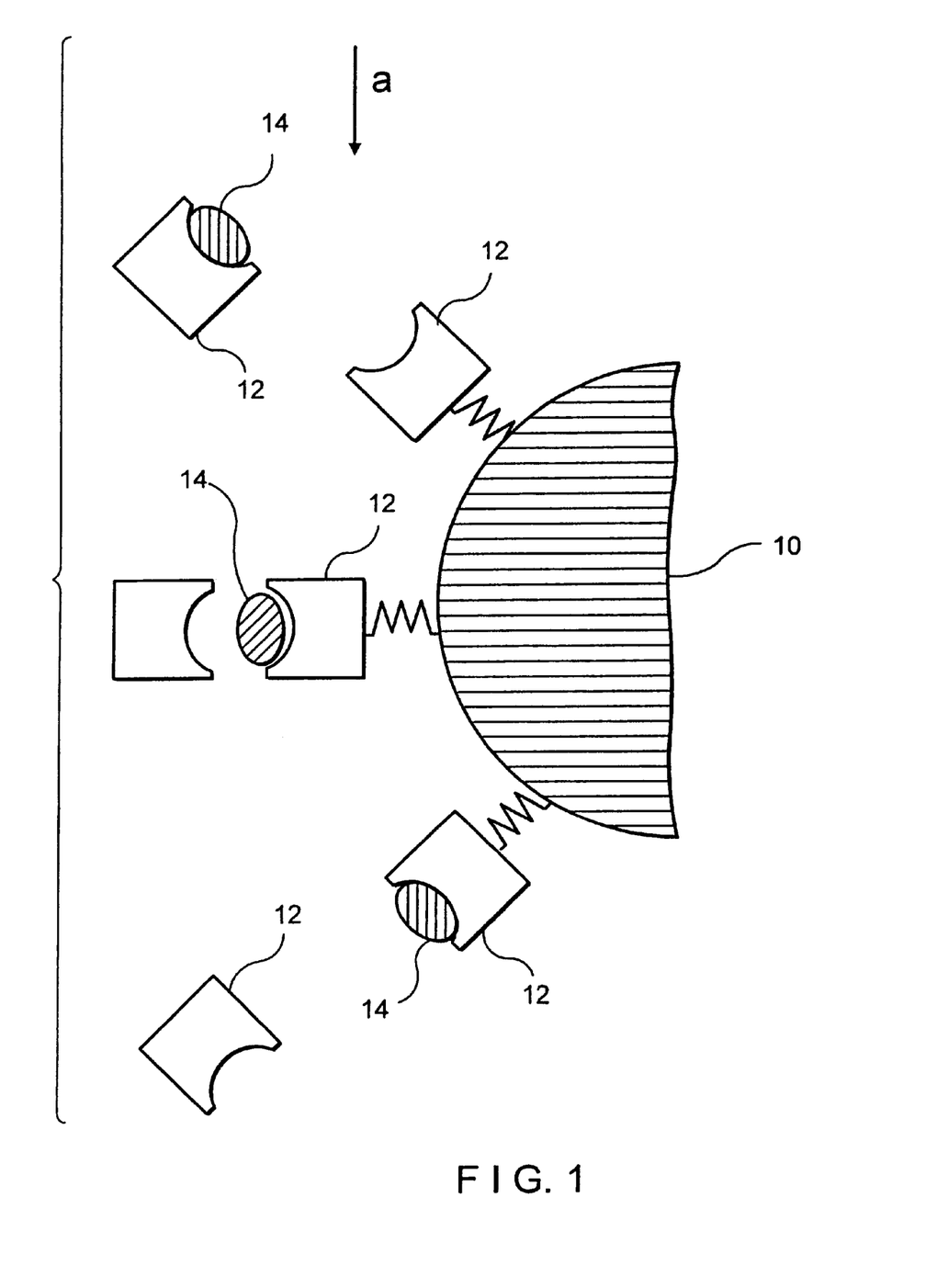
FIG. 1 schematically depicts the mechanism by which albumin-bound toxins are transferred to albumin molecules covalently bonded to a plastic substrate.

Example 1 according to the invention:

Plastic beads made of polymethacrylate or polyhydroxymethacrylate (e.g., EUPERGIT®, Röhm), for example, with a diameter of 10 to 500 m, are aminated and covalently coated with purified human albumin by means of suitable coupler reagents and packed in a column. The column prepared in this way is perfused with blood in an extracorporeal circulation. FIG. 1 shows a diagram of the mechanism. Human albumin 12 is covalently bonded to a plastic bead 10. Blood perfuses through the column in the direction of arrow a, so that toxin-bound or albumin-bound toxin 14 flows over the coated surface of the plastic bead. Following perfusion, the immobilized albumin 12 will adsorb toxins 14 having an affinity for albumin out of blood.

Figure 2:
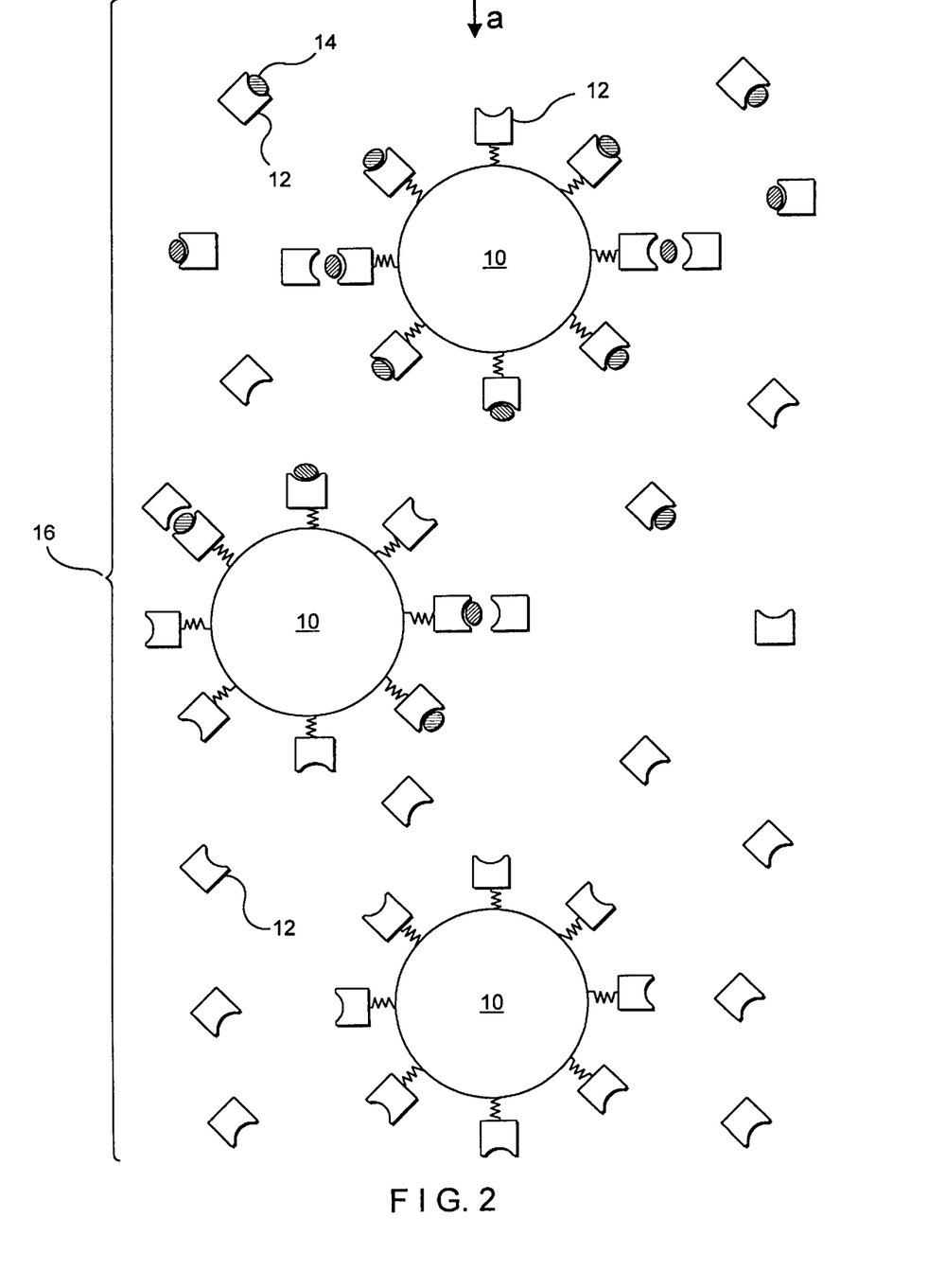
FIG. 2 schematically depicts albumin-bound toxins being removed from a solution.

FIG. 2 shows a column 16 through which a solution containing proteins flows in the direction of arrow d. This contains toxins 14 bound to albumin molecules 12. Toxins 14 are transferred to the surfaces of plastic beads 10 in the course of flowing past immobilized albumin 12. In the lower area of FIG. 2, albumin molecules 12 no longer have any toxins because all the toxins have been transferred. The mechanism shown in FIG. 2 corresponds to that explained in detail in Example 1.

1. Reaction of the covalent albumin coating 20 g oxirane acrylic resin beads (e.g., EUPERGIT®, Röhm) having an average diameter of approx. 200 microns and an average oxirane content of 0.2 mmol/g are aminated with 240 mL 13% ammonia solution for six hours at room temperature. After conclusion of the incubation and removal of all the ammonia solution by washing several times with distilled water (checking the pH), the beads are resuspended in 120 mL 30 mM sodium phosphate buffer, pH 4.8, and 1% (w/v) serum albumin (bovine serum albumin, free of fatty acid, Sigma). The batch is cooled to 4° C. to 6° C. in ice water. Coupling is performed by slowly adding 60 mL 5% (w/v) EDC solution in sodium phosphate buffer, pH4.8(EDC=1-ethyl-3-(3-dimethylaminopropyl)-carbodiimide). After adding the carbodiimide, the batch is agitated for four hours in ice water. Then the excess coupler reagent and protein are removed by washing repeatedly with ice-cold 0.9% sodium chloride solution. The beads treated in this way are then resuspended in 20 mM sodium phosphate buffer, pH 7.4, and the protein coupling yield is determined.

Typical coupling yields with BSA are 8 to 10 mg protein per gram of beads.

1.1. Adsorption of fatty acids from human plasma in the batch method

By centrifuging at 1500 g's for 15 minutes, plasma is obtained from freshly sampled whole blood, anticoagulated in ACD (ACD=sodium citrate/citrate-glucose solution), from healthy donors. The fatty acid content of the plasma is determined.

Albumin-acrylic resin beads prepared according to section 1 are sedimented in Eppendorf vessels, and the sodium phosphate buffer supernatant is removed. Precisely 0.1 mL sediment is then mixed with 0.5 mL plasma. The batch is incubated for one hour at 37° C. in an agitator. After incubation, the albumin-acrylic resin beads are sedimented again, and a sample is taken from the plasma supernatant for fatty acid determination. The remaining supernatant is removed and the beads are then washed six times with 1 mL 20 mM sodium phosphate buffer, pH 7.4, each time. The fatty acid content of the starting plasma, the plasma supernatant after adsorption and the fatty acid bound directly to the beads are measured. The fatty acid determination (S. Shimizu et al. 1980: Anal. Biochem. 107: 193–198) is performed by photometry using a commercial enzymatic color test (Boehringer, Mannheim). To determine the albumin-specific binding, control beads without the albumin coating were processed under similar conditions in all experiments.

Figure 3:
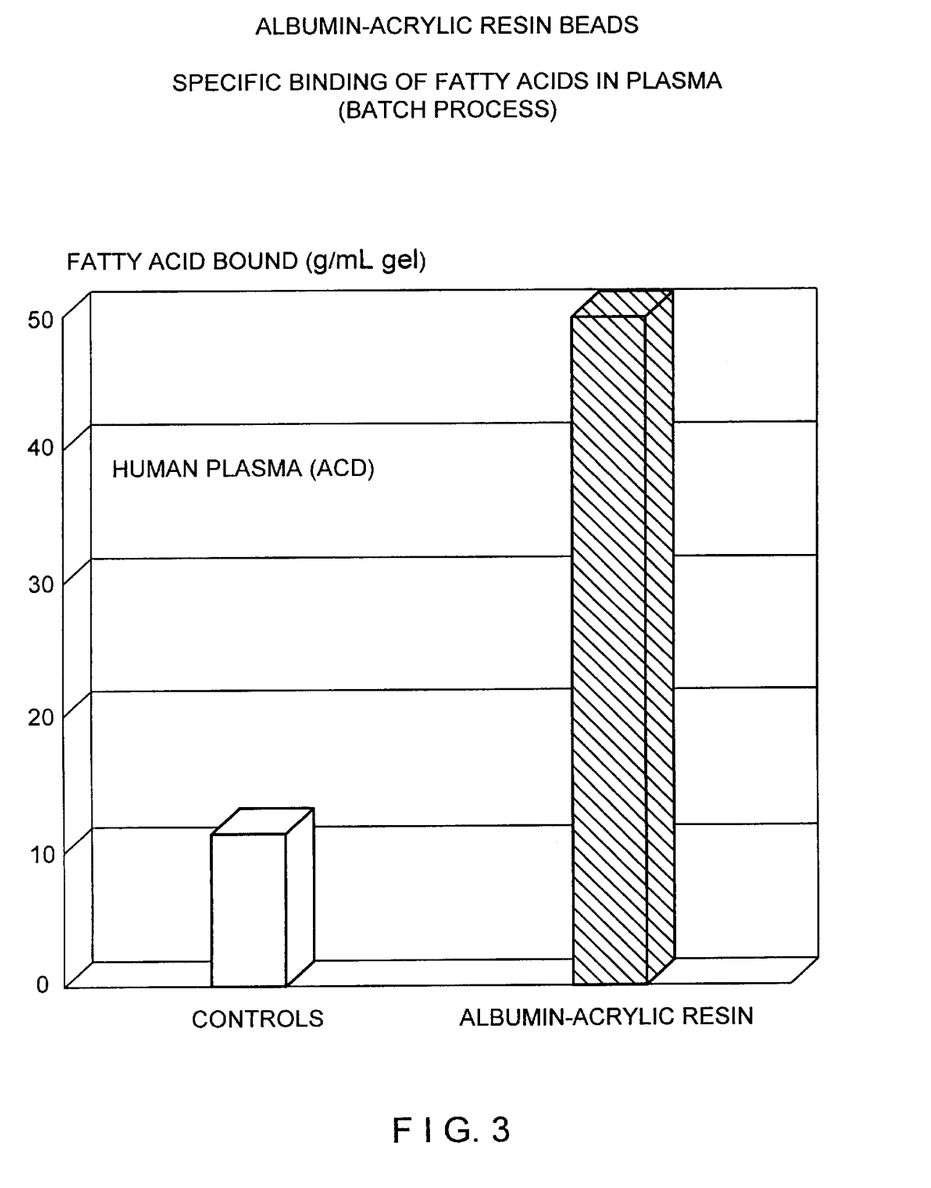
FIG. 3 is a graph demonstrating the binding of fatty acids in plasma to albumin-acrylic resin beads.

Table 1 and FIG. 3 summarize the results typically obtained with the experiment described here. A definite increase in binding of fatty acids is found with albumin-coated acrylic resin beads in comparison with the control beads.

Table 1: Adsorptive removal of fatty acids from human plasma with albumin-acrylic resin beads in a batch process.

| Type of specimen n = 10 | Extinction (546 nm) | Fatty acid concentration (mmol/L) | Bound fatty acid (g/mL beads) |
| --- | --- | --- | --- |
| Starting plasma | 0.927 | 0.88 | — |
| Plasma supernatant, albumin beads | 0.630 | 0.60 | — |
| Plasma supernatant control | 0.803 | 0.76 | — |
| Albumin beads | 0.430 | 0.25 | 49.6 |
| Contrdl beads | 0.098 | 0.05 | 11.3 |

1.2 Adsorption of endotoxins from human plasma by albumin-coated acrylic resin beads Exactly 5 mL albumin-acrylic resin beads, prepared as described in section 1, are packed into a column. The packed column, free of air bubbles as much as possible, is first perfused with 50 mL 0.5% (w/v) pyrogen-free deoxycholate solution (sodium deoxycholate, Fluka) at a flow rate of 5 mL/min. Any endotoxins adhering to the surfaces are removed with this step. Deoxycholate residues are removed with 1000 mL pyrogen-free 0.9% sodium chloride solution, and the column is then equilibrated with 50 mL 20 mM sodium phosphate buffer, pH 7.4. The washing operations and the equilibration are also performed with a flow rate of 5 mL/min. An aliquot of the last eluate is taken and tested for whether it is free of pyrogens. Plasma is obtained from heparinized (25 IU/mL Li-heparin) whole blood from healthy donors by centrifuging at 1500 g's for 15 minutes. Endotoxin (e.g., lipopolysaccharide from *E. coli*, 055:B5, Sigma) is added to the plasma immediately after obtaining the plasma, and the quantity of endotoxin is determined. In each instance 20 mL plasma with a total endotoxin content of 10,000 units (EU) are pumped through the column at a flow rate of 2 mL/min. The flow-through is collected. After the plasma has passed through the column, the column is rinsed with 20 mL 20 mM pyrogen-free sodium phosphate buffer. The rinsing solution is also collected.

The adsorption capacity of the albumin-acrylic resin beads is determined from the difference between the quantity of endotoxin used before the column and the quantity of endotoxin in the combined eluates after the column. Control experiments are conducted with a column of 5 mL acrylic resin beads without albumin coating under the same experimental conditions.

The endotoxin determination was performed in all experiments by means of a turbidimetric kinetic Limulus Amebocyte Lysate test (LAL test see: J. F. Remillard et al. 1987, in: S. W. Watson, J. Levin, T. J. Novitsky (eds.): "Detection of bacterial endotoxins with the Limulus Amebocyte Lysate Test." New York, Alan R. Riss, Inc., pp. 197–210).

Figure 4:
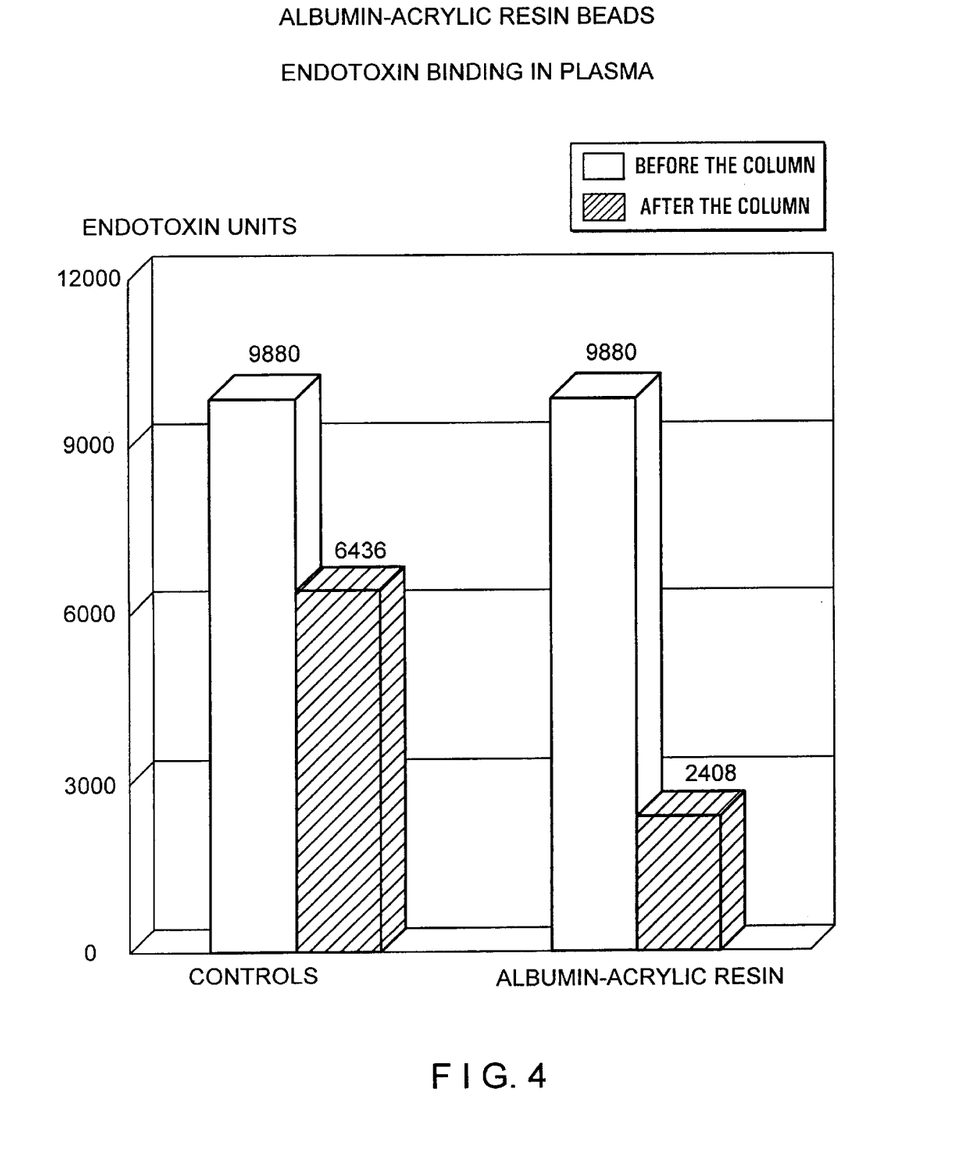
FIG. 4 is a graph demonstrating the binding of endotoxin to albumin-acrylic resin beads.

Table 2 and FIG. 4 summarize the results typically obtained in the experiments. In comparison with the control beads, the acrylic resin beads coated with albumin show a definite increase in endotoxin binding.

Table 2: Adsorptive removal of endotoxins from human plasma with albumin-acrylic resin beads

| Gel n = 6 | Total endotoxin before the column | Total endotoxin after the column | Binding (%) |
|---|---|---|---|
| Albumin-acrylic resin beads | 9,880 Eu | 2,408 EU | 76 |
| Control beads | 9,880 EU | 6,436 EU | 35 |

Covalent immobilization of albumin on surfaces of solid support materials is also especially advantageous because certain binding regions of the albumin molecule can be exposed due to the type of chemical coupling. For example, if the surface of the solid support contains amino groups, then the albumin molecule is preferentially bound with carboxyl groups on the support over structural areas when using carbodiimide as the coupler reagent. These regions are then no longer available for adsorption.

It can be seen that the albumin immobilized by carboxyl groups has strong binding properties with regard to the substances tested because it has a cationic character as a result of the immobilization.

The binding of albumin takes place by way of the amino groups of the support. Another advantage of the adsorber according to this invention is its hemocompatibility with whole blood. A measure of this is the reduction in platelets which remain adhering to the column. To demonstrate the improved whole blood compatibility, platelet adhesion in heparin plasma in the presence of LPS (500 pg/mL) is investigated below on the basis of a comparative experiment.

Figure 5:
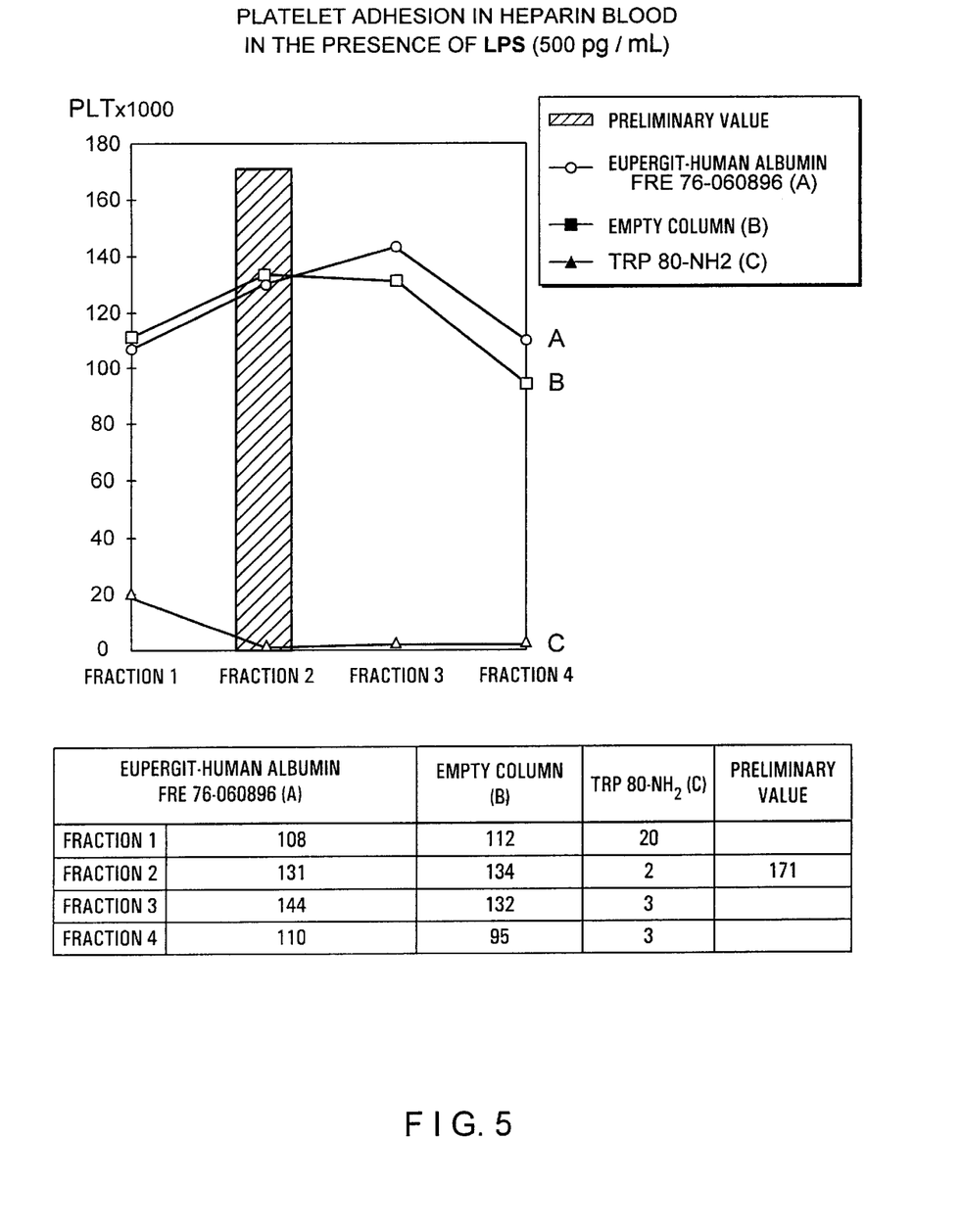
FIG. 5 is a graph depicting the adhesion of platelets in heparinized blood in the presence of LPS to three different substrates.

FIG. 5 shows as an example the properties of the albumin adsorber material according to this invention on the basis of the platelet loss of the perfused whole blood. The lower the drop in cell count with respect to the preliminary value, the better is the hemocompatibility of the adsorber. Curve A shows the drop in platelet count with the albumin adsorber material according to this invention. Curve B shows a control curve with a column without adsorber material. Curve C shows the drop in platelet count with an adsorber material of a known poor hemocompatibility.

Description of Experiment:

| Columns: | A: | Eupergit human albumin, lot FRE 76-060896 |
|---|---|---|
| | B: | empty column |
| | C: | TRP 80-NH$_2$ |
| Quantity of gel: | | 4 mL |
| Rinsing solution: | | 500 mL 0.9% NaCl solution |
| | | 500 mL 0.9% NaCl solution + 5 IU/mL sodium heparin |
| Rinsing flow: | | 900 mL/h |
| Blood volume: | | 12 mL |
| Heparin dosage: | | 25 IU/mL |
| Heparin used: | | sodium heparin, 5000 IU/0.2 mL, B. Braun Melsungen |
| Blood flow: | | 30 mL/h |
| Fractions: | | four fractions of 2 mL each |

Experimental Procedure:

Whole blood from healthy donors was taken from a tied-off arm vein and transferred to sterile Falcon PP tubes prepared with sodium heparin (heparin dosage: 25 IU/mL blood). The heparin blood specimens were then mixed with 500 pg/mL LPS from *E. coli* 055:B5 and preincubated for one hour at 37° C. on a rolling mixer. The columns packed with adsorber material were rinsed with the help of a Volumed infusion pump (Fresenius) before the experiment with the above-mentioned rinsing solutions. Before the start of the experiment, approx. 2 mL were taken (preliminary value) from the blood specimen. Then with the help of the Volumed pump, 12 mL blood was pumped through each column (see above for flow rate). Fractions of 2 mL each were collected in Eppendorf vessels. The cell count was determined in all specimens with the help of a Sysmex K1000.

Further inherent steam sterilization at 121° C. and 1 bar excess pressure, which is especially suitable for therapeutic purposes, is not tolerated by all materials, and in particular, no tolerance is expected with proteins. According to this invention, it has become possible to obtain this property of steam sterilizability by multipoint binding. The multipoint binding is achieved by selecting the molar ratios of the starting materials so that the molar groups of the support material are used in excess relative to the albumin concentration, preferably in a ratio of 50–500:1.

Another type of sterilization is also possible, e.g., with ethylene oxide or gamma radiation, but then the possibility cannot be ruled out that foreign substances or degradation materials might reach the adsorber material, which could later endanger the patient. Therefore, medical products today are increasingly sterilized only with superheated steam. This method is problematical when proteins are used because they are denatured by heat. Only through the multipoint binding according to this invention can denaturing be prevented and steam sterilizability be permitted.

Figure 6:
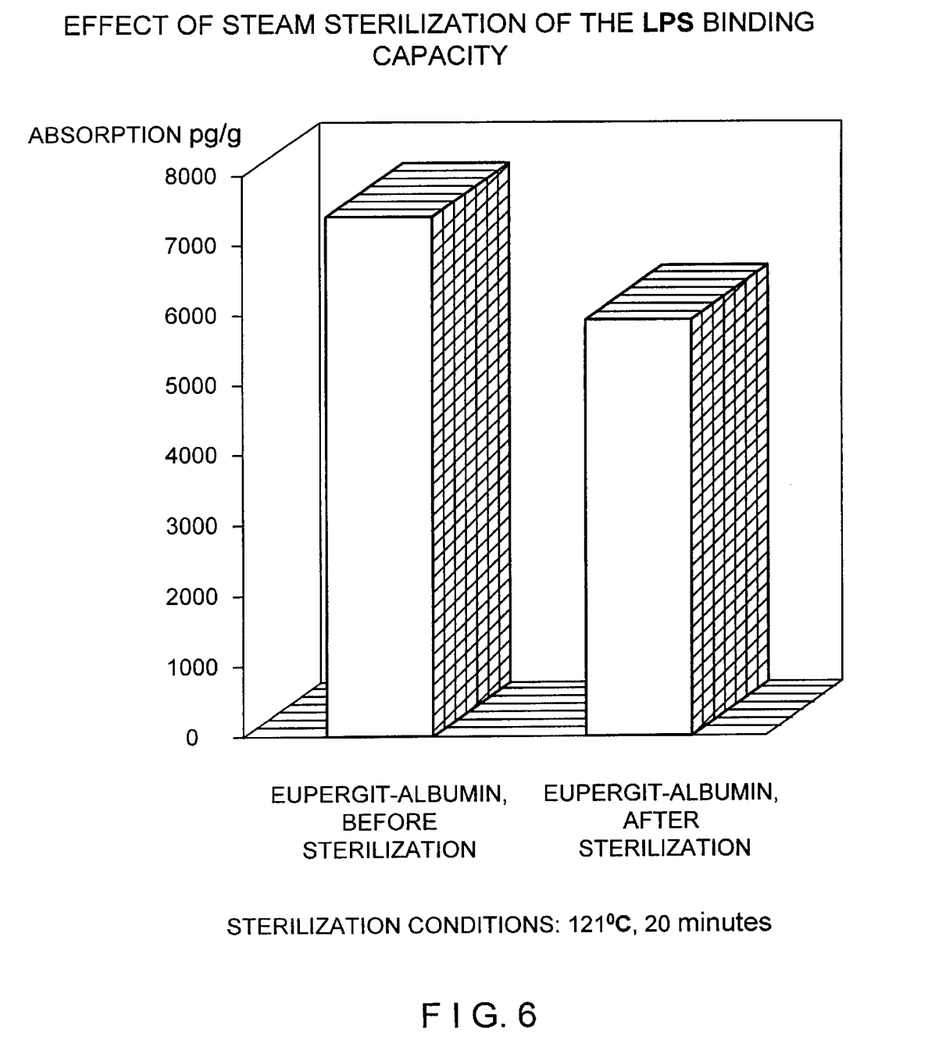
FIG. 6 is a graph demonstrating the effect of steam sterilization on the lipopolysaccharide binding capacity of an adsorbent material according to the present invention.

FIG. 6 shows a graphic plot of the lipopolysaccharide binding (endotoxin) before and after sterilization.

What we claim is:

1. A device for removing toxins from protein-containing solutions comprising albumin covalently bound to a biocompatible support material using peptide bonding.

2. The device of claim 1 wherein the device will remove protein-bound toxins from protein-containing solutions.

3. The device of claim 2 wherein the biocompatible support material is a plastic having amines or amides as a functional group.

4. The device of claim 3 wherein the plastic is selected from the group consisting of polyacrylates, polymethacrylates, polysulfone and polyether sulfone.

5. The device of claim 1 wherein the albumin is bound to the biocompatible support material by means of multipoint peptide binding.

6. The device of claim 1 wherein the biocompatible support material is in a form selected from the group consisting of beads, a flat or hollow fiber membrane, or a film.

7. The device according to claim 6 wherein the beads would have a diameter of from about 10 to 500 $\mu$m.

8. A device for removing protein-bound toxins from protein-containing solution comprising a biocompatible plastic support material coated with human albumin, wherein the albumin is bound to the support material by multipoint peptide bonding.

9. The device of claim 8 wherein the plastic of the support material is selected from the group consisting of polyacrylates, polymethacrylates, polysulfone and polyether sulfone.

10. A method for removing protein-bound toxins from protein-containing solutions comprising the steps of exposing the solution to a device consisting of a biocompatible plastic support material coated in human albumin, wherein the albumin is bound to the support material by multipoint peptide bonding, and flowing the solution over the human albumin immobilized on the support material, whereby the immobilized albumin adsorbs toxins having an affinity for albumin, and the toxins are transferred to the immobilized albumin and removed from the solution.

11. The method of claim 10 wherein the protein-containing solutions are selected from the group consisting of whole blood, plasma, or cell culture media.

* * * * *